US00PP32848P2

(12) United States Plant Patent
Hansen

(10) Patent No.: US PP32,848 P2
(45) Date of Patent: Feb. 23, 2021

(54) ***SALVIA* PLANT NAMED 'SNOW KISS'**

(50) Latin Name: ***Salvia pratensis* hybrid**
Varietal Denomination: Snow Kiss

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,944

(22) Filed: Aug. 20, 2020

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para

(57) ABSTRACT

The new and distinct cultivar of perennial *Salvia* plant named 'Snow Kiss' characterized by its white flower buds and large white flowers with a blush of pale purple densely arranged in verticils. The new plant has a dense habit with stiff, upright, heavily-branched stems showing persistent calyxes, a strong vigorous growth rate and dark olive-green foliage.

1 Drawing Sheet

Botanical denomination: *Salvia pratensis* hybrid.
Cultivar designation: 'Snow Kiss'.

STATEMENT REGARDING PRIOR DISCLOSURES UNDER 37 CFR 1.77(b)(6)

The first non-enabling disclosure, in the form of a catalog with a photograph and brief description was on Aug. 20, 2019 maintained by Gootjes-Allplant BV in The Netherlands. Gootjes-Allplant BV obtained their plants and all information about the new plant indirectly from the inventor. No plants of *Salvia* 'Snow Kiss' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Snow Kiss' or as the new plant. The new plant was selected from a cross under the direction of the inventor in the late spring of 2014 between 'Pretty in Pink' U.S. Plant Pat. No. 29,550 as the female or seed parent and the male or pollen parent is unnamed sibling of 'Pretty in Pink' (not patented). The cross was performed within the breeding area of a wholesale perennial nursery in Zeeland, Mich., USA. Seed was collected on Jun. 11, 2014 and sown at the same nursery. The new plant was initially evaluated in the summer of 2016 and assigned the breeder code 14-2-2 through the trial process prior to assigning the cultivar name.

The new *Salvia* was further evaluated and asexually propagated initially by division, by basal cuttings taken at the same nursery in Zeeland, Mich., USA in 2017 and later from shoot tip tissue culture. Evaluation of these and further cutting grown plants shows that *Salvia* 'Snow Kiss' continues to be stable and produce true to type plants in successive generations of asexual propagation.

SUMMARY OF THE INVENTION

Plants of *Salvia* 'Snow Kiss' have not been observed under all possible environmental conditions. The phenotype may vary somewhat with variations in environment such as temperature, nutrition and light intensity without, however, any variance in genotype.

*Salvia* 'Snow Kiss' can be closely compared to *Salvia* 'White Profusion'

U.S. Plant patent application Ser. No. 16/602,703, 'Florsalwhite' U.S. Plant Pat. No. 21,243, 'Bumblesnow' U.S. Plant Pat. No. 31,399, and 'Snow Hill' (not patented). 'White Profusion', 'Bumblesnow', 'Florsalwhite' and 'Snow Hill' all are *Salvia nemorosa* types with much smaller flowers. 'Snow Kiss' is slightly taller in flower habit than 'Snow Hill', 'White Profusion and 'Florsalwhite' and significantly taller than 'Bumblesnow'. 'Snow Hill' is much narrower in habit, and all the other comparison cultivars are more broad mounded than the new plant. All of the above comparison cultivars have pure white flowers without the pale purple blush. The female parent has similar-sized flowers, but of lavender pink flowers, and darker pink calyxes, deep purplish-red flower buds and grey-purple tinting of the peduncle.

The following characteristics in combination distinguish *Saliva* 'Snow Kiss' as a new and distinct cultivar from all other cultivars known to the inventor:

1. Large white flowers with a pale purple blush densely arranged in verticils;
2. Stiff, upright, chartreuse, heavily-branched stems;
3. White flower buds with a blush of pale purple;
4. Dense, rounded, strong, vigorous and winter-hardy habit;
5. Rugose, dark olive-green foliage.

BRIEF DESCRIPTION OF THE DRAWINGS

The photographs of the new plant demonstrate the unique traits and the overall appearance of *Salvia* 'Snow Kiss'. The colors are as accurate as reasonably possible with color reproductions. Variation in ambient light spectrum, source and direction may cause the appearance of minor variation in color. The plant used in the photographs was a three-year old plant grown in an open, full-sun trial garden at a wholesale perennial nursery in Zeeland, Mich. with supplemental water and fertilizer when needed. Plant growth regulators have been used in greenhouse grown trials only.

DETAILED BOTANICAL DESCRIPTION

Figure 1:
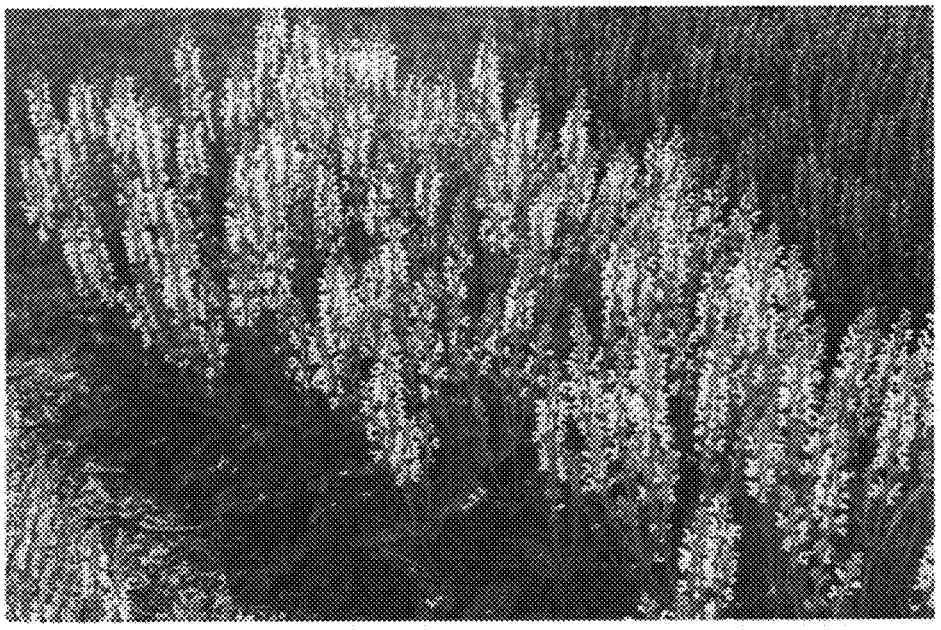
FIG. 1 shows the plant habit in full flower in a landscape.
Figure 2:
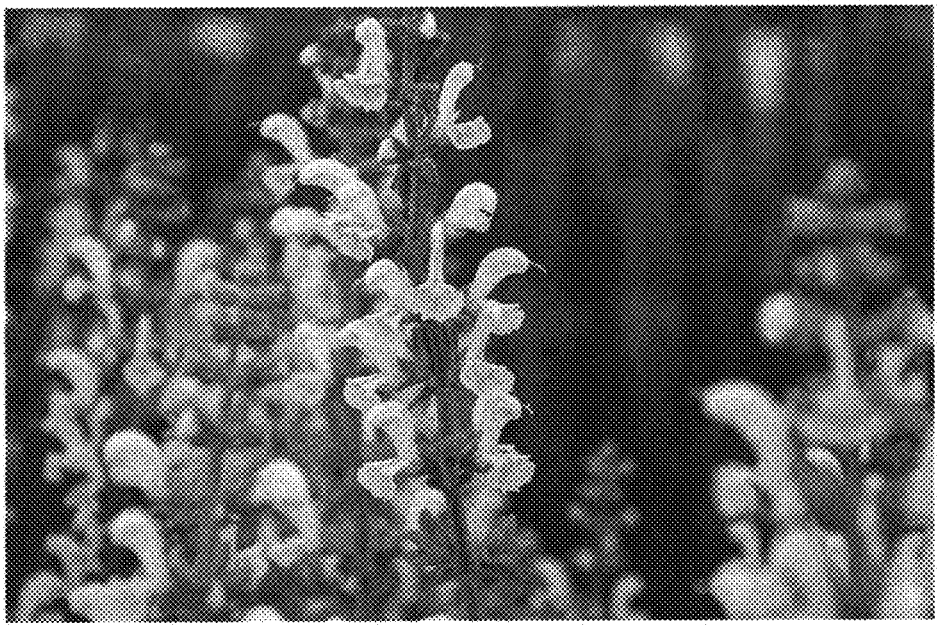
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Snow Kiss' has not been observed under all possible environments. The phenotype may vary slightly with different growing environments such as temperature, light, fertility, soil pH, moisture and plant maturity levels, but without any change in the genotype. The following observations and size descriptions are based on three-year old plants growing in an outdoor full-sun trial garden at a wholesale perennial nursery in Zeeland, Mich. and greenhouse forced two-year old plants. Plants were given supplemental water and fertilizer and plant growth regulators were used for the greenhouse trials only.

Botanical classification: *Salvia pratensis* hybrid (Linnaeus);

Parentage: Female or seed parent 'Pretty in Pink'; male or pollen parent unnamed sibling to 'Pretty in Pink';

Plant habit: Winter-hardy herbaceous perennial; multi-stemmed, compact, rounded, with mostly basal foliage, and flowers in several tightly arranged in verticils on branched upright racemes displayed above foliage; in flower with panicles about 55 cm tall and about 60 cm wide at the fullest point; foliage extends up the stems about 26 cm tall from soil and 50 cm wide below flower;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite, simple, rugose, lanceolate; margin crenate and crenulate; glabrous and matte abaxial and adaxial surfaces; acute apex and base cordate to auriculate with lobes frequently overlapping; leaf blades about 14.0 cm long and 6.0 cm across, decreasing in size distally; average about 11.0 cm long and 4.5 cm across; faint sage fragrance;

Foliage color: Young adaxial surface between RHS 146A and RHS 146B, abaxial surface nearest RHS 146B; mature adaxial surface between RHS NN137B and NN137A, abaxial surface between RHS 147B and RHS 137B;

Venation: Reticulate; impressed on adaxial side and costate on abaxial side; pubescent abaxial, puberulent adaxial;

Vein color: Adaxial midrib nearest RHS 145C, primary and secondary veins nearest RHS 145C toward midrib and gradually darkening to between RHS 138A and RHS 138B; abaxial midrib nearest RHS 145C, primary veins nearest RHS 145C and secondary veins nearest RHS 145C gradually darkening to nearest RHS 146C toward leaf margin;

Petiole: Concavo-convex; pubescent abaxial and along margin, sparsely puberulent adaxial; to about 8.0 cm long and 5.0 mm wide, average 4.5 cm long and 4.0 mm wide at base;

Petiole color: Adaxial and abaxial surfaces nearest 146D;

Inflorescence: Verticillate with flowering generally beginning at lower verticils and advancing up the scape, but not all flowers at each verticil opening at the same time giving the effect of a scape being in continuous flower for longer periods; average distance between verticils about 12.0 mm, greater proximally and less distally; attitude with midline projected about 10 degree angle above horizontal and hood petal about 45 degree angle above horizontal; self-cleaning, petals not persistent; flowering beginning late spring for about six weeks with limited repeating if initial scapes removed;

Flower longevity: About four days on the plant or as cut flower;

Fragrance: None detected under present growing conditions;

Flower buds one to two days prior to anthesis: Shape is rounded on top and slightly concave below, with rounded apex; pubescent; about 10.0 mm long, 5.0 mm tall and 3.0 mm wide;

Bud color: Exposed dorsal petals nearest RHS NN155D, ventral petals nearest RHS NN155D blushed with nearest RHS N75D; abaxial calyx between RHS 146D and RHS N144A with veins nearest RHS 146C;

Flowers: Perfect, bilabiate corolla with arcuate hooded upper lip and tri-lobed lower lip; about 18.0 cm long, 20.0 mm tall and 7.5 mm wide, fused into tube in the proximal 8.0 mm; clustered at verticils;

Petals: Bilabiate corolla; upper hood petal arcuate and flattened side to side vertically, lower petal labiate with crenate rounded apex and base fused with labium;

Hood (upper) petal: Minutely pubescent abaxial, glabrous adaxial; about 19.0 mm long, 12.0 mm tall and 3.0 mm across;

Labium (lower) petal: Consisting of three lobes, two proximal lobes about 3.0 mm long and 2.5 mm wide at base with rounded apex; center lobe with rounded emarginate apex, about 7.0 mm long 10.0 mm wide; center lobe slightly concaved upwards; total labium about 15.0 mm long, 8.0 mm wide at the widest portion across lobes and 5.0 mm tall;

Petal color: Abaxial and adaxial hood petal nearest RHS NN155D; lower labium petal abaxial nearest RHS NN155D with center labium lobe lightly blushed with between RHS 76D and RHS N75D in center and lower abaxial tube distal fusion for about 3 mm lightly blushed with between RHS 76D and RHS N75D; abaxial dorsal calyx tube and adaxial calyx tube nearest RHS NN155D;

Androecium: Two, fused with labium, contained within hood petal except when triggered by pollinator;

*Filament*.—Glabrous, fused about 7.0 mm from base of labium petal; curved around inside of hood petal; about 12.0 mm long and less than 0.5 mm diameter with a 2.0 mm trip mechanism at base; color nearest RHS NN155D with very faint blushing nearest RHS N75D in distal region before anther.

*Anther*.—Glabrous, oblong, about 3.0 mm long and 1.0 mm diameter; longitudinal, dorsifixed; color nearest RHS 11C.

*Pollen*.—Abundant; globose; less than 0.1 mm circumference; color nearest RHS 12B.

Gynoecium: One, curved around inside of hood petal;

*Style*.—About 24.0 mm long and less than 0.5 mm diameter; color nearest RHS NN155D and faintly blushed distally about 5.0 mm before stigma split with nearest RHS 77D.

*Stigma*.—Bifurcate and curved in the terminal 2.0 mm; apex pointed; color nearest RHS 77A.

*Ovary*.—Superior; color more green than RHS 145A and more yellow than RHS 138B.

Fruit: Nutlet, one to four per flower; rounded, about 1.5 mm diameter; color darker than RHS 200A;

Calyx: Five sepals, three upper and two lower, campanulate, apex acute; fused in basal 4.0 mm; tube about 7.0 mm long and 6.0 mm tall at and 3.0 mm wide at apex; lower set bifurcate in terminal 2.5 mm; upper set of trifurcate in distal 1.0 mm;

Calyx color: Variable with light intensity, abaxial between RHS 146D and RHS N144A with veins of nearest RHS 146C; adaxial between RHS N144A and RHS 146C with darker veins of RHS 146B toward apex;

Bracts: Each verticil subtended by two opposite nearly lanceolate bracts; apex acuminate, base truncate, margin entire and ciliolate; coarsely wavy to bent downward toward apex; glabrous above and below; bract size up to 12.0 mm long and 7.0 mm wide, decreasing distally;

Bract color: Adaxial surface nearest RHS 146B with midrib and base nearest RHS 145C; abaxial between RHS 146C and RHS 146D;

Peduncles: Raceme; quadrangular in cross section; about 15 per plant; strong; upright; to about 55 cm tall and 5.0 mm across; puberulent to glandular; branches in lower two to four nodes, upright at 60 degrees above horizontal or greater; branches to about 20.0 cm long and 3.0 mm across; average internode distance about 5.0 cm;

Peduncle color: Nearest RHS 146B along longitudinal center and corners nearest RHS N144A;

Pedicels: Cylindrical; puberulent to glandular; about 1.5 mm long and 0.5 mm diameter; puberulent to glandular; nearly horizontal at flower anthesis;

Pedicel color: Nearest RHS N144A;

Disease and pest resistance: Plants of *Salvia* 'Snow Kiss' perform best with adequate moisture and good drainage and are hardy from USDA zone 3 to 8. Resistant to diseases and pests beyond that common to *Salvia* has not been noted.

It is claimed:

1. The new and distinct perennial *Salvia* plant named 'Snow Kiss' as herein described and illustrated useful for landscaping as a specimen plant, en masse or as a cut flower.

* * * * *